US00PP31030P2

(12) United States Plant Patent
Morgan

(10) Patent No.: US PP31,030 P2
(45) Date of Patent: Nov. 5, 2019

(54) ***GENTIANA* PLANT NAMED 'FI0304123'**

(50) Latin Name: ***Gentiana* hybrid**
Varietal Denomination: Fi0304123

(71) Applicants: The New Zealand Institute for Plant and Food Research Ltd., Auckland (NZ); John Moffat, Southland (NZ)

(72) Inventor: Edmond Robert Morgan, Auckland (NZ)

(73) Assignees: John Moffatt, Southland (NZ); THE NEW ZEALAND INSTITUTE FOR PLANT AND FOOD RESEARCH LTD., Auckland (NZ)

( * ) Notice: Subject to any disclaimer, the term of this patent is extended or adjusted under 35 U.S.C. 154(b) by 0 days.

(21) Appl. No.: 15/732,959

(22) Filed: Jan. 17, 2018

(51) Int. Cl.
*A01H 5/02* (2018.01)
*A01H 6/40* (2018.01)

(52) U.S. Cl.
USPC ..... Plt./433

(58) Field of Classification Search
USPC ..... Plt./433
CPC ... A01H 5/02; A01H 5/00; A01H 6/40; A01H 6/00
See application file for complete search history.

(56) References Cited

U.S. PATENT DOCUMENTS

PP27,706 P3 * 2/2017 Morgan ..... A01H 5/02 Plt./433

OTHER PUBLICATIONS

Upov Pluto Plant Variety Database Jan. 8, 2019, retrieved on Jan. 8, 2019, retrieved from the Internet at www3.wipo.int/pluto/user/en/index.jsp, one page. (Year: 2019).*

* cited by examiner

*Primary Examiner* — June Hwu
(74) *Attorney, Agent, or Firm* — Penny J. Aguirre

(57) ABSTRACT

A new cultivar of *Gentiana* plant named 'Fi0304123' that is characterized by its flower corollas that are purple-blue in color, its lateral branching that is suitable for pot plant production, lateral flowering branches on the lower protion of the main stems, and its late flowering period.

2 Drawing Sheets

Botanical classification: *Gentiana* hybrid.
Varietal denomination: 'Fi0304123'.

BACKGROUND OF THE INVENTION

The present invention relates to a new and distinct cultivar of *Gentiana* and will be referred to hereafter by its cultivar name, 'Fi0304123'. 'Fi0304123' represents a new *Gentiana*, an herbaceous perennial grown for landscape use.

The new Invention arose from an ongoing controlled breeding program in Aukland, New Zealand. The objective of the breeding program is to develop new cultivars of *Gentiana* with unique flower colors and plant habits suitable for the potted plant production.

The Inventor made a controlled cross in summer of 2007 between unnamed and unpatented proprietary plants from the Inventor's breeding program as both the female and male parents. The Inventor selected 'Fi0304123' as a single unique plant amongst the seedlings that resulted from the above cross in April of 2018.

Asexual propagation of the new cultivar was first accomplished under the direction of the Inventor by tissue culture using meristem tissue in Palmerton North, Auckland, New Zealand in April of 2008. Asexual propagation by tissue culture has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Fi0304123' as a new and unique cultivar of *Gentiana*.

1. 'Fi0304123' exhibits flower corollas that are purple-blue in color.
2. 'Fi0304123' exhibits lateral branching that is suitable for pot plant production.
3. 'Fi0304123' exhibits lateral flowering branches on the lower portion of the main stems.
4. 'Fi0304123' exhibits a late flowering period.

The female parent plant of 'Fi0304123' differs from 'Fi0304123' in having flowers that are red in color. The male parent plant of 'Fi0304123' differs from 'Fi0304123' in having flowers that are more blue in color. 'Fi0304123' can be most closely compared to the *Gentiana* cultivars 'RI0405128' (U.S. Plant Pat. No. 27,706) and 'Marsha' (U.S. Plant Pat. No. 16,562). 'RI0405128' differs from 'Fi0304123' in having a shorter plant height, in lacking flowering branch production on the lower nodes of the main stems, and in having flowers that are more violet in color. 'Marsha' differs from 'Fi0304123' in having flower corollas that are more blue in color on the outer surface.

BRIEF DESCRIPTION OF THE DRAWINGS

The accompanying colored photographs illustrate the overall appearance and distinct characteristics of the new *Gentiana*. The photographs were taken of plants 18 months in age as field grown in Reeuwijk, The Netherlands (with stems placed in a container for the photographs).

Figure 1:
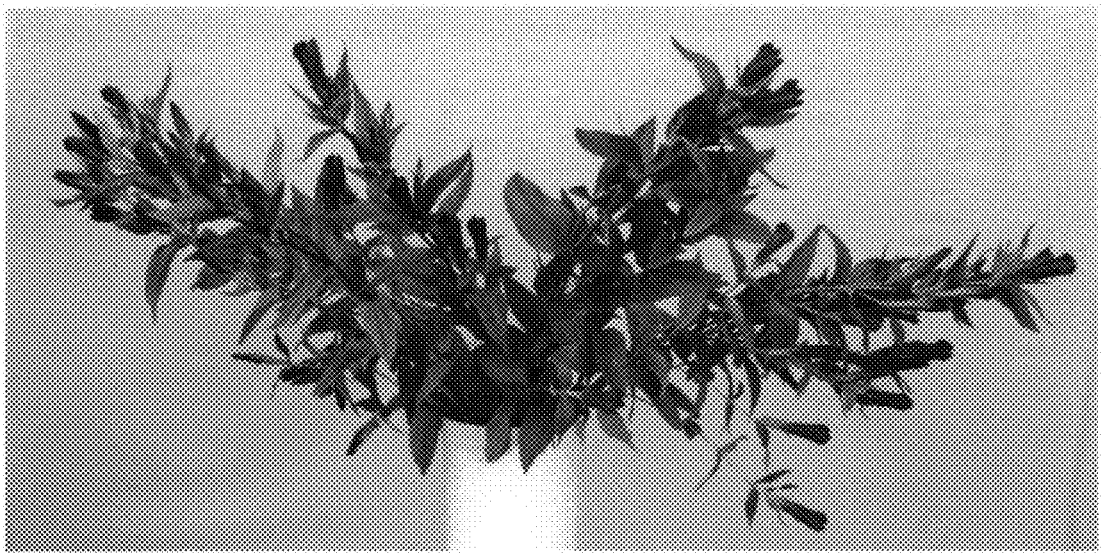
FIG. 1 provides a view of the flowering branches of 'Fi0304123'.
Figure 2:
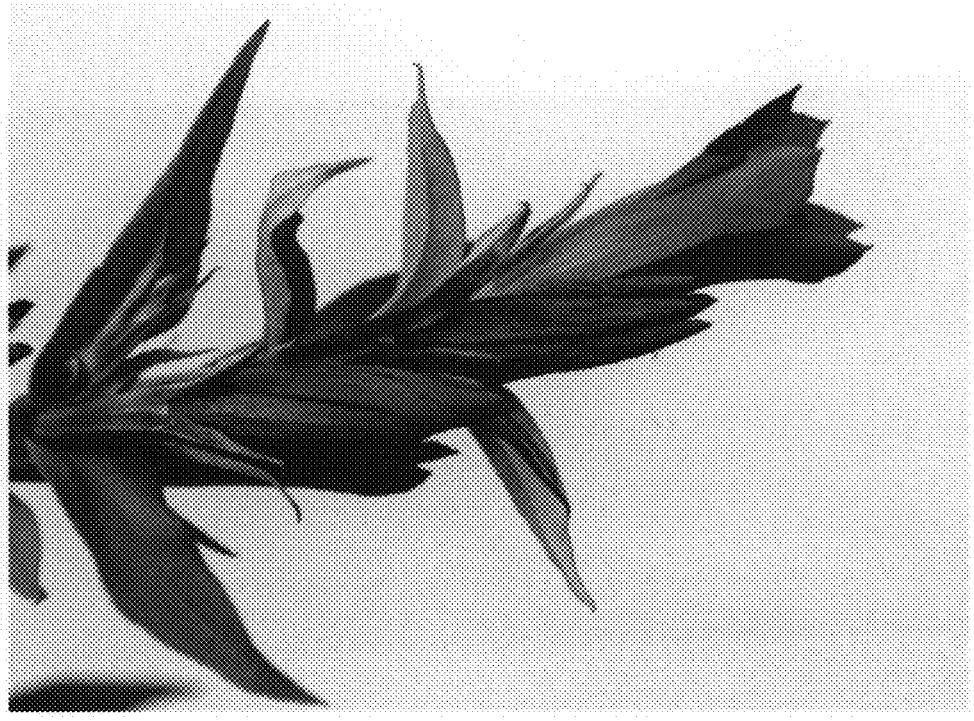

The photograph in FIG. 2 provides a close-up view of the flowers of 'Fi0304123'.

Figure 3:
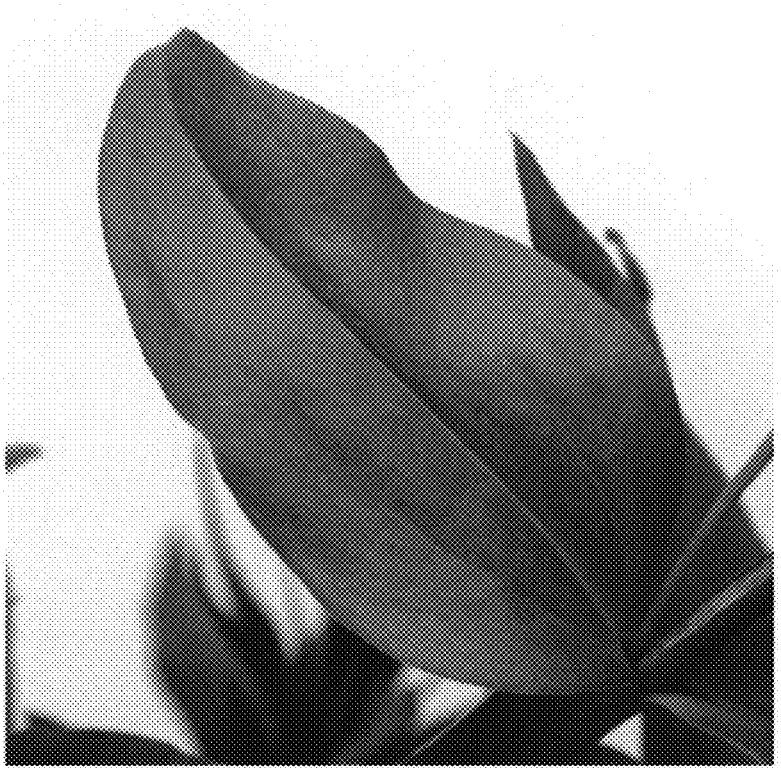

The photograph in FIG. 3 provides a close-up view of a leaf of 'Fi0304123'.

The colors in the photographs are as close as possible with the photographic and printing technology utilized and the color values cited in the detailed botanical description accurately describe the colors of the new *Gentiana*.

DETAILED BOTANICAL DESCRIPTION OF THE PLANT

The following is a detailed description of 18 month-old plants of the new cultivar as field grown in Reeuwijk, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Late blooming; 5 weeks from late summer into August in New Zealand.

*Plant type*.—Herbaceous perennial.

*Plant habit*.—Upright, narrow obovate.

*Height and spread*.—An average of 89 cm in height (soil level to top of foliar plane), 93 cm in height (soil level to top of floral plane) and 40 cm in width.

*Cold hardiness*.—At least in U.S.D.A. Zone 6.

*Diseases and pests*.—No susceptibility or resistance to diseases or pests has been observed.

*Root description*.—Fine and fibrous.

*Propagation type*.—Tissue culture.

*Root development*.—An average of 6 months to fully root in a 9-cm container from a tissue culture plug.

*Growth rate*.—Moderate to high.

Stem description:

*Stem shape*.—Rounded.

*Stem color*.—Young; 145B, mature; 145B tinged 187B.

*Stem size*.—An average of 85 cm in length and 3.5 mm in diameter.

*Stem surface*.—Slightly glossy.

*Stem aspect*.—Main stems held in an average angle of 20° and lateral stems held at an average angle of 30° to main branch.

*Internode length*.—An average of 5.3 cm.

*Branching habit*.—Main branches grow from base with lateral branches, an average of 8 main basal stems and 2 lateral branches per main stem, number of side shoots with only one node is few and the number of side shoots with more than one node is many.

Foliage description:

*Leaf shape*.—Ovate.

*Leaf division*.—Simple.

*Leaf base*.—Cuneate.

*Leaf apex*.—Acute.

*Leaf venation*.—Parellel, upper surface 143A, lower surface 145B.

*Leaf margins*.—Entire.

*Leaf attachment*.—Sessile.

*Leaf arrangement*.—Opposite.

*Leaf surface*.—Upper and lower surface; smooth, glabrous and slightly glossy.

*Leaf color*.—Young upper surface; between 143A and 143B, young lower surface; 145A, mature upper surface; between 137B and 143A, mature lower surface; between 146D and 147C.

*Leaf number*.—Average of 30 (15 pairs) per main stem.

*Leaf size*.—Average of 10.3 cm in length and 3.8 cm in width, the position of the longest leaves are present on the lower third of the stem.

Flower description:

*Flower type*.—Axillary and terminal tubular flowers, solitary or in pairs.

*Flower fragrance*.—None.

*Flower lastingness*.—Average of 10 days on plant, persistent.

*Flowering sequence*.—Flowering on terminus and axillary nodes is primarily simultaneous.

*Flower buds*.—Narrowly elliptic in shape, average of 1.3 cm in diameter (including sepals), 0.5 cm in diameter (excluding sepals) and 4.3 mm in length, surface is smooth, glabrous and matte, color; 79A, fading towards the base to N77C, immature calyx 145A to 145D, tinged 177B.

*Flower quantity*.—An average of 50 per stem.

*Flower aspect*.—Held upright.

*Flower shape*.—Tubular.

*Flower size*.—An average of 2.3 cm in height and diameter, 6.2 cm in length, throat diameter 1.2 cm, flower tube length 3.1 cm, flower tube diameter 1.5 cm.

*Peduncles*.—None present.

*Pedicels*.—An average of 2 mm in length and 1 mm in width, held upright relative to stem, strong, smooth, glabrous and slightly glossy surface, 144B in color.

*Petal description*.—5, oblong in shape, an average of 3.1 cm in length and 1.3 cm in width, 80% of lower portion is fused into a tubular shape, margin is entire, apex is acute, upper and lower surface is glabrous, smooth and velvety in appearance, curvature of the corolla lobes in straight, color opening upper surface; N89A to N89B, opening lower surface N89A, fully open upper surface; N89B to N89C with stripes absent, fully open lower surface; N89A and N92D flushed with 79A to 79B, upper and lower surface fading to N89A and N186B, flower throat; N89C, flower tube; inner (upper) surface 145D with a sparse amount of stripes N92D, outer (lower) surface 86B and N92D.

*Paracorolla*.—Absent.

*Calyx form*.—Campanulate, 3.5 cm in length, 2.6 cm in diameter.

*Sepals*.—Rotate, fused into a campanulate shape, an average of 5, average of 3.5 cm in length and 2.5 mm in width, narrow oblong in shape, margin is entire, apex is free and acute, base is fused, upper 55% free, upper and lower surface is smooth and dull, color; when opening and fully open upper surface 143A, lower half 145C, when opening lower surface 145A with upper half tinged N200B to N200C, fully open lower surface 144B to 145A with upper half tinged N200B to N200C.

Reproductive organs:

*Gynoecium*.—Pistil; 1, 3 mm in length, stigma; 5 mm in diameter, decurrent, split in two, 151D in color, style; 1.5 mm in length, 145C in color, ovary; 145C in color.

*Androecium*.—Stamens; 5, filaments; 3.4 cm in length, 157D, color fading towards the base to 145D, anther; 3 mm in length, 1.5 mm in width, 160D in color, pollen; low in quantity, 2B to 2C in color.

*Fruit and seed*.—None has been observed to date.

It is claimed:

1. A new and distinct cultivar of *Gentiana* plant named 'Fi0304123' as herein illustrated and described.

* * * * *